United States Patent
Moore

(10) Patent No.: US 6,792,809 B1
(45) Date of Patent: Sep. 21, 2004

(54) SELF-ALIGNING TURBINE DISC INSPECTION APPARATUS

(75) Inventor: Charles C. Moore, Hibbs, PA (US)

(73) Assignee: Siemens Westinghouse Power Corporation, Orlando, FL (US)

( * ) Notice: Subject to any disclaimer, the term of this patent is extended or adjusted under 35 U.S.C. 154(b) by 0 days.

(21) Appl. No.: 10/428,694

(22) Filed: May 2, 2003

(51) Int. Cl.[7] .............................................. G01N 29/04
(52) U.S. Cl. .............................. 73/618; 73/624; 73/583
(58) Field of Search .............................. 417/61; 73/116, 73/866.5, 618–624, 623, 634, 583; 324/240–243

(56) References Cited

U.S. PATENT DOCUMENTS

| | | | |
|---|---|---|---|
| 4,304,133 A | * 12/1981 | Feamster, III | ................ 73/633 |
| 4,502,331 A | 3/1985 | Singh et al. | |
| 4,586,380 A | * 5/1986 | Patterson | ..................... 73/623 |
| 4,741,203 A | 5/1988 | Willaman et al. | |
| 5,383,355 A | 1/1995 | Baleras et al. | |
| 5,670,879 A | 9/1997 | Zombo et al. | |
| 5,781,007 A | 7/1998 | Partika et al. | |
| 5,959,211 A | * 9/1999 | Wagner et al. | ................ 73/634 |
| 6,065,344 A | 5/2000 | Nolan et al. | |
| 2002/0088282 A1 | 7/2002 | Zayicek et al. | |

\* cited by examiner

*Primary Examiner*—Robert Raevis

(57) ABSTRACT

A self-aligning turbine disc inspection apparatus (30) for positioning a non-destructive examination sensor (38) proximate the disc web surface (20) of a turbine rotor assembly (10). The apparatus supports the sensor at a proper height above a support surface (34) while simultaneously providing passive freedom of movement in X, Y and theta directions so that the sensor is free to follow the slight movements of the web surface as the rotor assembly is rotated on a test stand. The freedoms of movement are provided by a first sled (52) rolling on a base (42), by a theta alignment assembly (62) rotating on the first sled, and a second sled (54) sliding on the theta alignment assembly. A vertical drive assembly (48) attached to the second sled provides a selectable height. The sensor may be moved across the disc web surface by a motorized slide (82) attached to a head assembly (46) attached to the vertical drive assembly. A radial centering assembly (70) makes contact with the rotor assembly at two spaced-apart points to ensure that the inspection apparatus is positioned at a bottom-dead-center location.

13 Claims, 5 Drawing Sheets

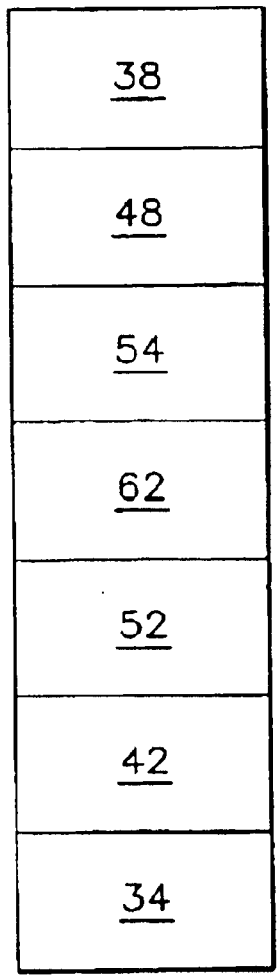
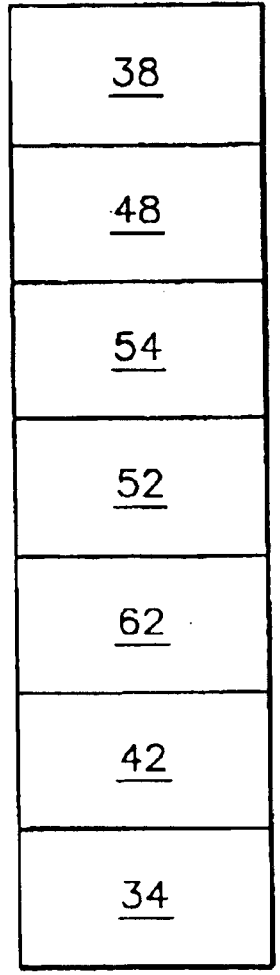
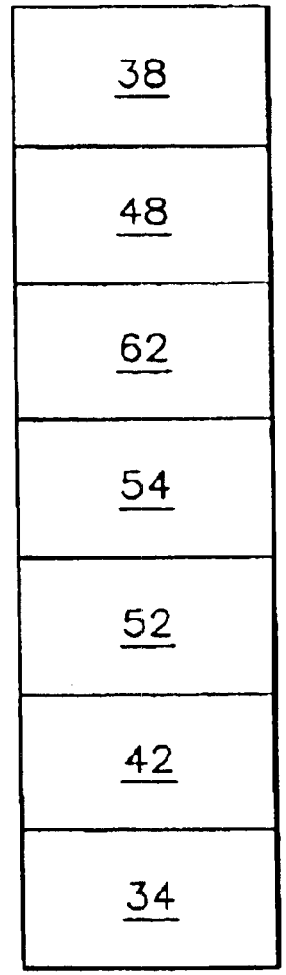
*FIG. 6A*  *FIG. 6B*  *FIG. 6C*

SELF-ALIGNING TURBINE DISC INSPECTION APPARATUS

FIELD OF THE INVENTION

This invention relates generally to the field of turbine inspections, and more specifically to an apparatus for inspecting the discs of a turbine rotor assembly.

BACKGROUND OF THE INVENTION

High reliability of power generation equipment is an ongoing goal of the electric utility industry. Turbine parts are routinely inspected during planned plant outages in order to detect operationally induced discontinuities before they progress to a point where they may risk component failure. One portion of the turbine that is routinely inspected is the blade root area of the turbine rotor assembly.

A prior art steam turbine rotor assembly 10 is illustrated in cross-sectional view in FIG. 1. The rotor assembly 10 includes a shaft 12 on which are mounted a plurality of wheels or discs 14 that are coaxial with the shaft 12, with the shaft 12 extending through a bore formed at the center of each disc 14. A plurality of blades 16 are mounted to the periphery of each disc 14, generally by inserting a root portion of the blade (not shown) into a mating groove 18 formed along the circumference of the disc 14, as shown in FIG. 2. It is known to scan the disc web surface 20 with an ultrasonic transducer or other type of sensor in order to search for cracks in the region of the groove 18. Such prior art inspections are normally conducted with the rotor assembly 10 removed from the turbine casing and supported on a test stand at an inspection location. The ultrasonic sensor is mounted on an elongated arm that is manually guided between adjacent blades 16 to position the sensor against the disc web surface 20 while the rotor assembly 10 is slowly rotated on the test stand. One may appreciate that such manual positioning of the sensor is strenuous and subject to the potential for positional inaccuracy. Accordingly, an improved scheme for positioning the sensor during a turbine rotor disc inspection is desired.

SUMMARY OF THE INVENTION

An apparatus for positioning a sensor proximate a surface of a disc of a turbine rotor assembly is described herein as including: a sensor assembly; and an alignment correction assembly supporting the sensor assembly from a support surface and providing passive freedom of movement there between.

An apparatus for positioning a sensor proximate a surface of a disc of a turbine rotor assembly as the rotor assembly is supported over a support surface is described herein as including: a means for supporting a sensor in a vertical direction; and a means for providing a passive freedom of movement between the sensor and the support surface about a horizontal plane.

A turbine rotor inspection apparatus is described herein as including: a base; a first sled supported vertically on the base and free to move in a first direction along a horizontal plane; a theta alignment assembly supported vertically on the first sled and free to rotate in the horizontal plane; a second sled supported vertically on the theta alignment assembly and free to move in a second direction perpendicular to the first direction in the horizontal plane; a vertical drive assembly supported by the second sled and having a selectable vertical length; a head assembly connected to the vertical drive assembly; and a sensor connected to the head assembly.

BRIEF DESCRIPTION OF THE DRAWINGS

These and other advantages of the invention will be more apparent from the following description in view of the drawings that show:

FIGS. 6A, 6B and 6C are schematic illustrations of the location of a theta alignment correction assembly relative to a base, a first sled and a second sled in three alternative embodiments.

DETAILED DESCRIPTION OF THE INVENTION

Figure 3:
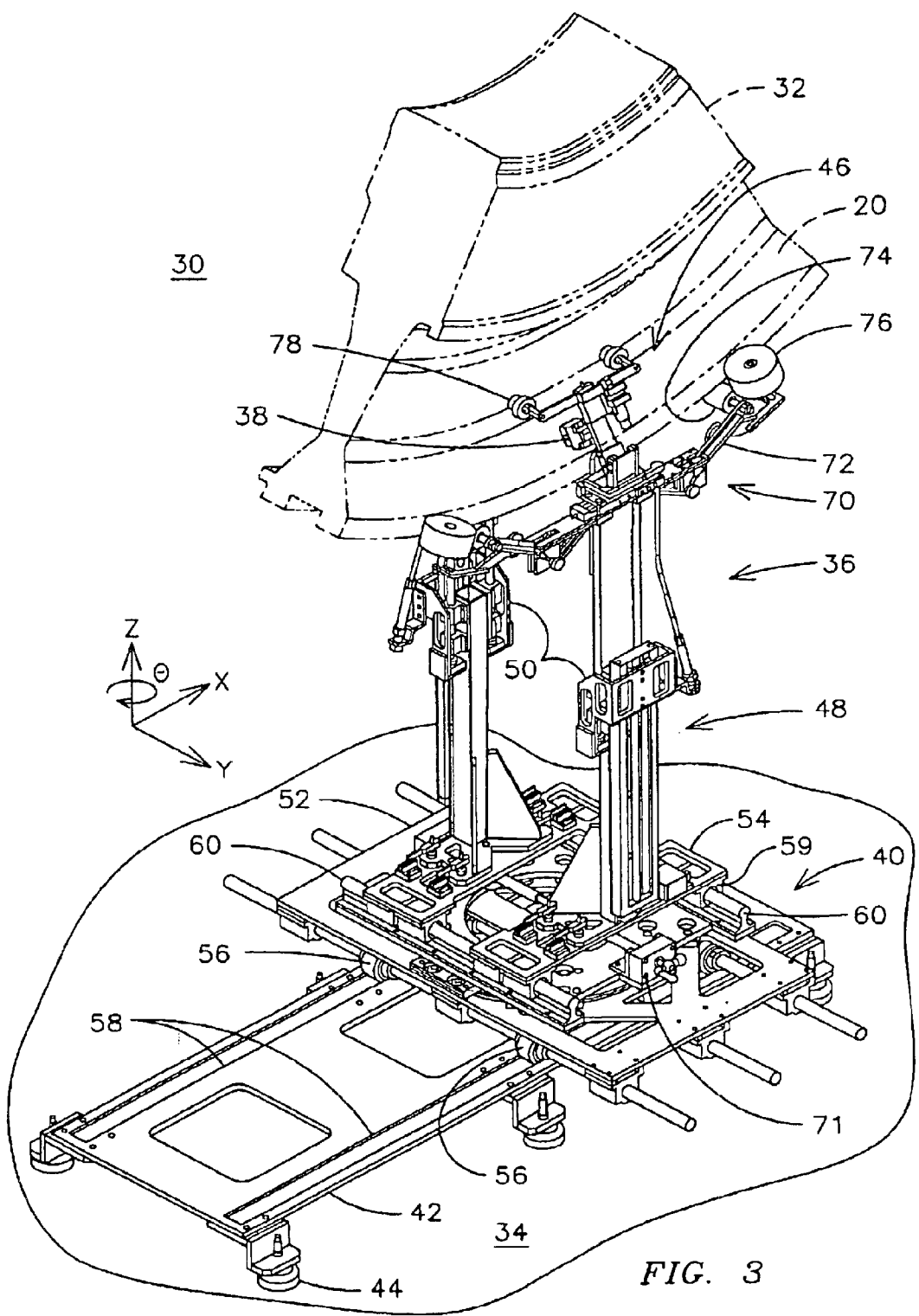
FIG. 3 is a perspective view of self-aligning turbine disc inspection apparatus in position under a turbine disc.

A turbine disc inspection apparatus 30 is shown in FIG. 3 in position for conducting an inspection of a turbine rotor disc 32. The turbine rotor disc 32 is removed from the turbine casing and is supported above a support surface 34 in an inspection stand with rotational drive capabilities (not shown). The inspection apparatus 30 includes a sensor assembly 36 for grasping and positioning a sensor 38 such as ultrasonic transducer 38 proximate the disc web surface 20. The sensor assembly 36 is supported from the support surface 34 by an alignment correction assembly 40 that provides vertical support for the sensor assembly 36 while at the same time allowing for a passive freedom of movement of the sensor assembly 36 relative to the support surface 34. The term "passive freedom of movement" is used herein to mean a degree of freedom of movement wherein movement is permitted under the influence of a reactive force generated by the spatial interaction of the inspection apparatus 30 with the support surface 34 and the turbine rotor disc 32 and without the necessity for a motorized or otherwise powered reconfiguration of the inspection apparatus 30. The turbine disc inspection apparatus 30 may include a base 42 that provides the interface with the support surface 34 through a plurality of height-adjustable feet 44 for securing the apparatus 30 on an uneven support surface 34. The support surface 34 will typically be a horizontal floor at a power plant location.

The sensor assembly 36 includes a head assembly 46 and a vertical drive assembly 48. The vertical drive assembly 48 includes vertical slide assemblies 50 that are mechanically driven to any of a plurality of positions for vertically supporting the head assembly 46 and sensor 38 at a selected height above the support surface 34. The vertical drive assembly 48 may include a lift system (not shown) such as electrical stepper motors, hydraulic cylinders, mechanical ratchet, etc.

The alignment correction assembly 40 allows the sensor assembly 36 the freedom to move linearly in X and Y directions along a horizontal plane as well as to rotate in a theta direction in the horizontal plane about a vertical axis Z, while at the same time providing vertical support. Other embodiments may have alignment correction assemblies that provide positional support in at least one direction while allowing passive freedom of movement in one or several other directions. The linear movements are accomplished in this embodiment by a pair of sleds 52, 54. First sled 52 is supported by base 42 through the rolling contact between wheels 56 and linear track 58 to provide vertical support while allowing linear movement in the X direction. Second sled 54 is supported above first sled 52 through sliding contact between a plurality of slide blocks 59 and rails 60 to provide vertical support while allowing linear movement in the Y direction. Any known type of wheels, rollers, bearings, lubricants, sliders, etc. may be used in various embodiments to accomplish the functions of vertical support and freedom of horizontal movement.

Figure 4:
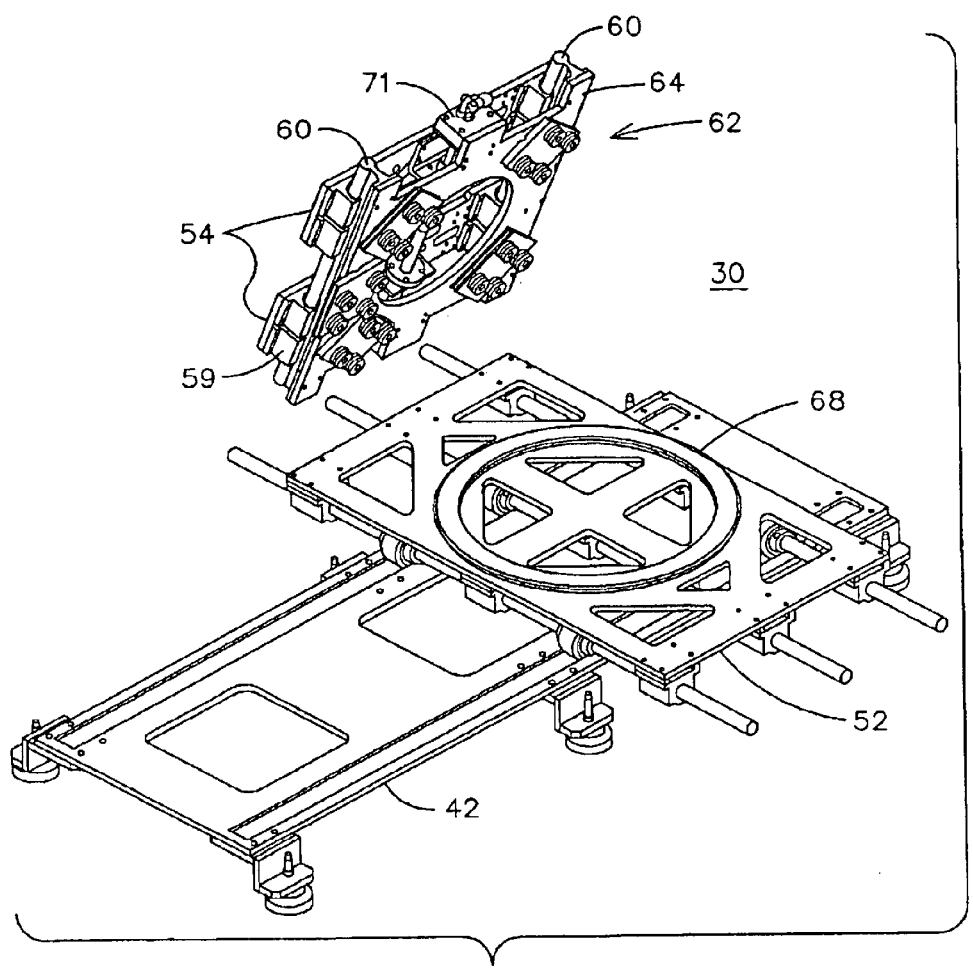
FIG. 4 is a partial exploded view of the turbine disc inspection apparatus of FIG. 3.

Freedom of rotational movement in the theta direction is provided by a theta alignment assembly 62, as may seen more clearly in the partial exploded view of turbine disc inspection apparatus 30 provided in FIG. 4. The theta alignment assembly 62 includes a frame 64 and attached rollers 66 for curvilinear movement along an arcuate track 68, which is disposed upon first sled 52. In this embodiment, the theta alignment assembly 62 is disposed between the first sled 52 and the second sled 54, as illustrated schematically in FIG. 6A. In other embodiments, the theta alignment assembly 62 may be located between the base 42 and the first sled 52 (FIG. 6B), or between the second sled 54 and the vertical drive assembly 48 (FIG. 6C), or at any other point in the load path between the support surface 34 and the sensor 38.

Vertical drive assembly 48 includes two parallel slide assemblies 50 that are horizontally separated by a distance that is adjustable by an operator. An axial centering apparatus 71 such as a lead screw and gear mechanism drives the two vertical slide assemblies 50 relative to each other along rails 60. This capability is useful when placing the inspection apparatus 30 in position for performing an inspection, as is described more fully below.

At least one of the two head assemblies 46 includes a radial centering assembly 70. The radial centering assembly 70 includes opposed arms 72 having rollers 74 at respective distal ends. The arms 72 may be adjustable to a range of angles relative to horizontal to make contact with discs 20 having a range of diameters. With the radial centering assembly 70 set to the proper diameter for disc 32, and the vertical drive assembly 48 withdrawn to a retraced position, the turbine disc inspection apparatus 30 is moved to a position underneath a turbine rotor disc 32. At this point, axial centering apparatus 71 is set so that the spacing between the opposed head assemblies 46 permits the head assemblies 46 to be raised upward on opposite sides of the disc 32 without mechanical interference. The vertical slide assemblies 50 are then extended to lift the head assemblies 46 to a desired height to place the sensor 38 proximate the disc web surface 20. As the vertical slide assemblies 50 are raised, one of the rollers 74 will contact the disc 32 first if the inspection apparatus 30 is not directly under the disc 32. As the vertical slide assemblies 50 continue to be raised, the roller 74 that is in contact with the disc 32 will generate a reactive force that has a horizontal component, causing the roller 74 to roll along the disc 32. In this manner, the floating action of the first sled 52 across base 42 will allow the vertical drive assembly 48 to position itself directly beneath the vertical radial centerline of the disc 32, i.e. bottom dead center, at which time both rollers 74 of the radial centering assembly 70 will make contact with the disc 32 at two spaced-apart points on opposed sides of a bottom-dead-center position, and the resulting horizontal force will go to zero.

Most turbine rotors include one or more permanent markings that indicate radial locations along the rotor. Such markings may be stamped on an end surface 86 of the rotor, for example. Prior to performing an inspection, the rotor assembly 10 may be rotated to a known position, such as having a zero degree mark positioned directly downward at a bottom-dead-center position. The sensor 38 is then positioned at the bottom-dead-center location using the apparatus 30 and method described above. Sensor measurements taken thereafter can be accurately associated with a specific angular position on the rotor assembly 10, thereby eliminating the positional uncertainty associated with prior art inspection techniques. This precision may be especially useful when comparing inspection results obtained over a period of time.

Once at the head assemblies 46 are at the desired vertical height, the axial slide apparatus 71 is activated to close the distance between the opposed head assemblies 46. This will cause one of the sets of lower ball casters 76, which may be located on the radial centering assembly 70 (as illustrated) or on the head assembly 46 (not shown) to make contact with the disc 32, thus halting further advance of the associated vertical slide assembly 50. Continued operation of the axial slide apparatus 71 draws the opposed vertical slide assembly 50 closer to the halted vertical slide assembly 50 until the rotor disc 32 is captured between the opposed sets of lower ball casters 76.

Figure 1:
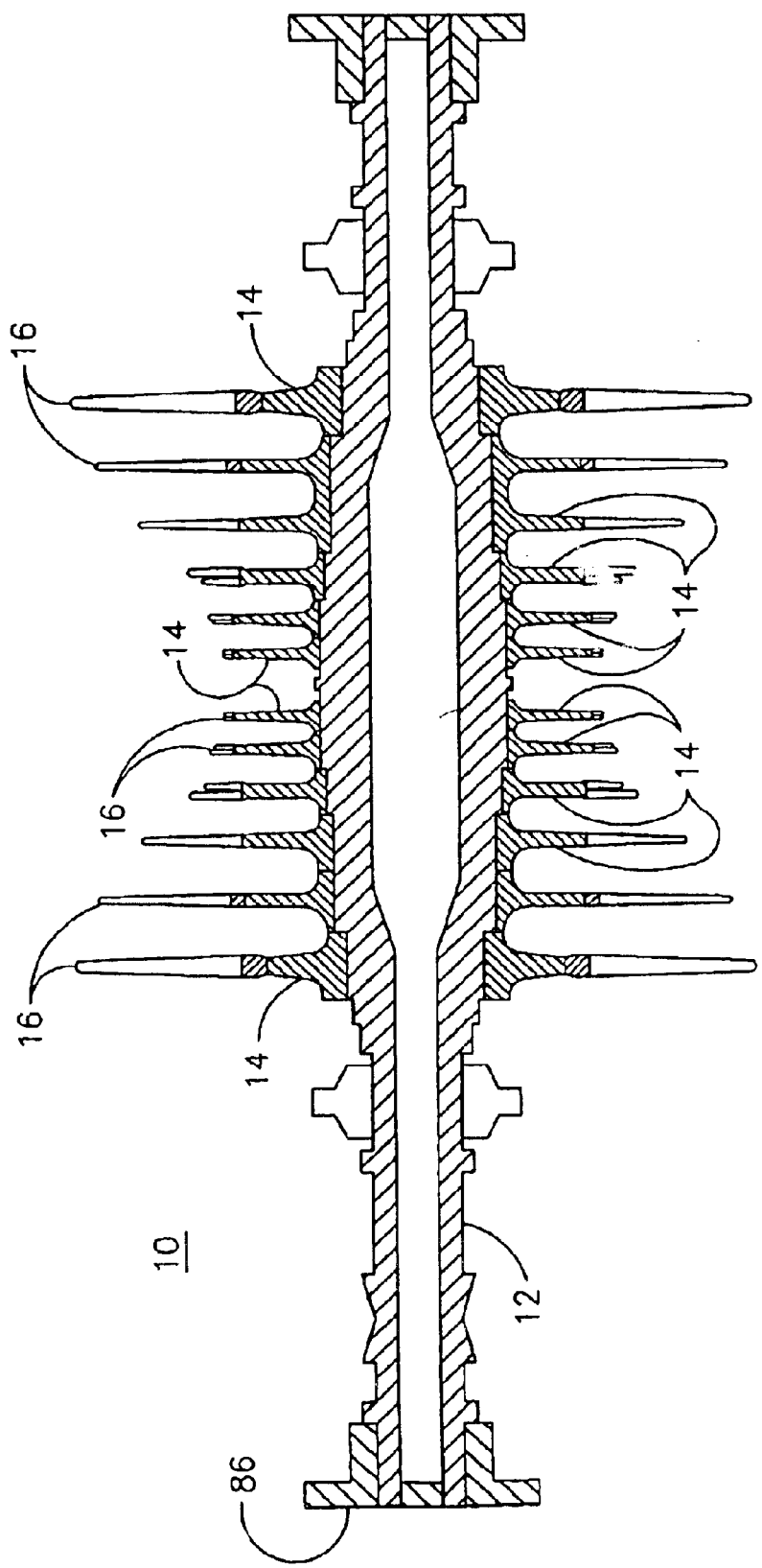
FIG. 1 is a cross-sectional view of a prior art steam turbine rotor assembly.
Figure 2:
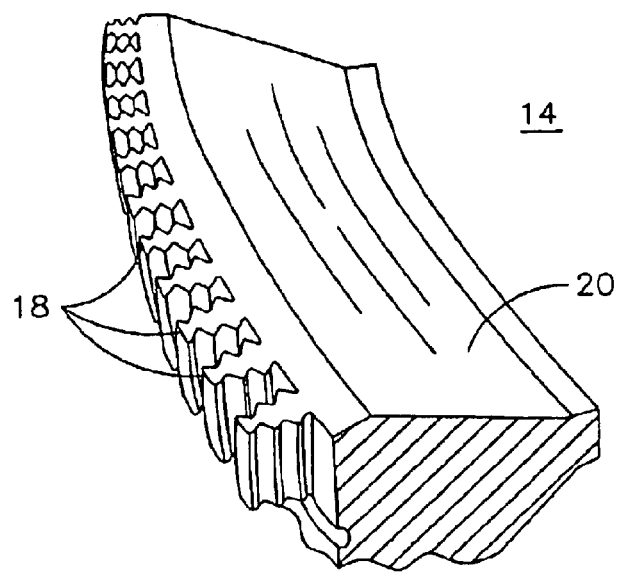
FIG. 2 is partial perspective view of a disc of the prior art steam turbine rotor assembly of FIG. 1.
Figure 5:
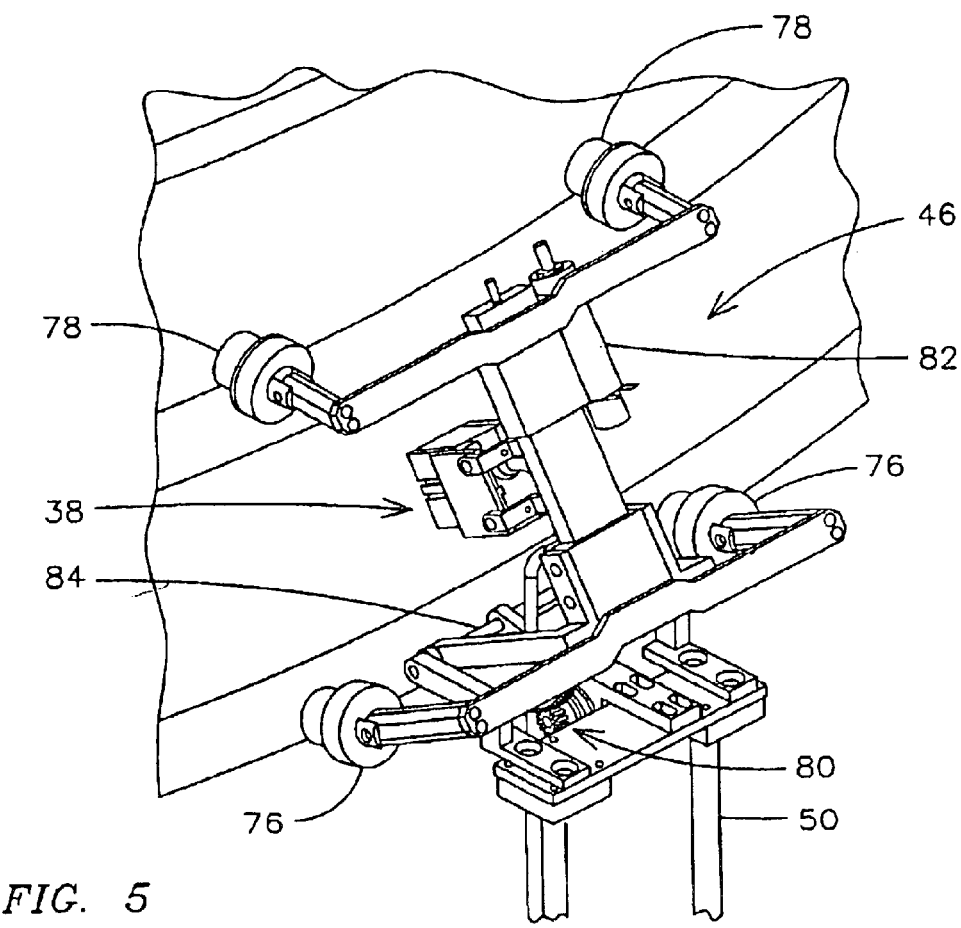
FIG. 5 is a perspective view of a further embodiment of a head assembly of a turbine disc inspection apparatus.

During the above-described initial positioning steps, the head assemblies 46 are maintained in a vertical position directly above the vertical slide assemblies 50. The following steps may be best understood with reference to FIG. 5, which is a perspective view of one head assembly 46 illustrated without a radial centering assembly and with the lower ball casters 76 being attached directly to the head assembly 46. Once the disc 32 is captured between the lower ball casters 76, the head assemblies 46 are released to rotate about a horizontal axis such as hinge 84 so that the upper ball casters 78 contact the disc 32. The head assembly 46 may be initially held in the vertical position by a latch (not shown), with a rotary damper 80 being provided to urge the head assembly 46 softly against the disc 32 when unlatched. The spring bias affect of the rotary damper 80 ensures that the upper and lower ball casters 76, 78 remain in contact with the disc web surface 20 during rotation of the disc 32. FIG. 5 also illustrates a motorized slide 82 that is used to move the sensor 38 across the disc web surface 20 to accomplish the inspection of the entire area of interest as the disc 32 is rotated.

While the preferred embodiments of the present invention have been shown and described herein, it will be obvious that such embodiments are provided by way of example only. Numerous variations, changes and substitutions will occur to those of skill in the art without departing from the invention herein. For example, the frame of reference used throughout this application is horizontal and vertical since in a preferred embodiment the support surface 34 is a horizontal floor and the inspection apparatus 30 and turbine rotor disc 32 are supported vertically from the floor. One may appreciate that other frames of reference may be used in other embodiments and that the terms "horizontal" and "vertical" should not be construed as limiting but rather as indicating relative directions in a three dimensional environment. Furthermore, directions X and Y are described as being perpendicular in a horizontal plane, with Z being vertical and theta being rotation around the Z-axis. A similar relationship among these directions may be envisioned for other "horizons" in other embodiments.

I claim as my invention:

1. An apparatus for positioning a sensor proximate an arcuate surface of a disc of a turbine rotor assembly, the apparatus comprising:

a sensor assembly; and an alignment correction assembly supporting the sensor assembly from a support surface and providing passive freedom of movement about at least two linear axes of movement there between, such that the sensor can substantially follow the arcuate surface of the disc of the turbine rotor assembly.

2. An apparatus for positioning a sensor proximate a surface of a disc of a turbine rotor assembly, the apparatus comprising:

a sensor assembly; and an alignment correction assembly supporting the sensor assembly from a support surface and providing passive freedom of movement there between, the alignment correction assembly further comprising:

a base;

a first sled supported vertically and horizontally in Y and theta directions by the base and free to move horizontally in a X direction relative to the base;

a theta alignment correction assembly supported vertically and horizontally in the X and Y directions by the first sled and free to rotate in the theta direction relative to the first sled; and a second sled connected to the sensor assembly and supported vertically and horizontally in the Y and theta directions by the theta alignment correction assembly and free to move horizontally in the Y direction relative to the theta alignment correction assembly.

3. The apparatus of claim 2, further comprising a wheel rotatably supported on the first sled for rolling contact with the base.

4. The apparatus of claim 2, further comprising a roller supported on the theta alignment correction assembly for rolling contact with an arcuate track disposed on the first sled.

5. The apparatus of claim 2, further comprising:

a rail connected to the theta alignment correction assembly; and a slide block connected to the second sled and comprising an opening for receiving the rail.

6. An apparatus for positioning a sensor proximate a surface of a disc of a turbine rotor assembly, the apparatus comprising:

a sensor assembly; and an alignment correction assembly supporting the sensor assembly from a support surface and providing passive freedom of movement there between;

wherein the sensor assembly further comprises a pair of opposed arms extending apart a predetermined distance for contacting the disc at two spaced-apart points on opposed sides of a bottom-dead-center position.

7. An apparatus for positioning a sensor proximate a surface of a disc of a turbine rotor assembly, the apparatus comprising:

a sensor assembly; and an alignment correction assembly supporting the sensor assembly from a support surface and providing passive freedom of movement there between;

wherein the alignment correction assembly further comprises:

a base;

a first sled vertically supported by the base and providing passive freedom of movement there between along an X direction; and a second sled vertically supported by the first sled and providing passive freedom of movement there between along a Y direction.

8. The apparatus of claim 7, wherein the alignment correction assembly further comprises a theta alignment correction assembly providing a passive freedom of rotational movement, the theta alignment correction assembly disposed between one of the base and the first sled, the first sled and the second sled, and the second sled and the sensor assembly.

9. The apparatus of claim 7, wherein the theta alignment correction assembly further comprises a roller connected to the second sled and traversing an arcuate path for providing vertical support and passive freedom of rotational movement there between.

10. The apparatus of claim 7, wherein the alignment correction assembly further comprises:

a track disposed on the base; and a wheel rotatably attached to the first sled for riding on the track.

11. The apparatus of claim 10, wherein the alignment correction assembly further comprises a roller attached to the second sled for traversing an arcuate track on the first sled to provide passive freedom of rotational movement there between.

12. The apparatus of claim 1, wherein the sensor assembly further comprises a vertical member having a selectable vertical length.

13. The apparatus of claim 12, wherein the sensor assembly further comprises a radial centering assembly comprising arms extending in opposed radial directions for contacting the disc at two spaced-apart circumferential points.

* * * * *